United States Patent [19]

Beecher

[11] Patent Number: 4,551,888
[45] Date of Patent: Nov. 12, 1985

[54] BAG SHUT-OFF CLAMP

[75] Inventor: William H. Beecher, Elmhurst, Ill.

[73] Assignee: Illinois Tool Works Inc., Chicago, Ill.

[21] Appl. No.: 535,121

[22] Filed: Sep. 23, 1983

[51] Int. Cl.[4] .............................................. A44B 21/00
[52] U.S. Cl. .................................. 24/30.5 P; 24/518;
24/520; 24/543; 24/562; 128/346
[58] Field of Search ................ 24/518, 562, 487, 543,
24/520, 198, 199, 30.5 R, 30.5 P, 17 AP, 115 L,
132 WL; 128/346

[56] References Cited

U.S. PATENT DOCUMENTS

| 1,186,656 | 6/1916 | Fridolph | 24/520 |
|---|---|---|---|
| 1,327,761 | 1/1920 | Kestenman | 24/518 |
| 2,261,825 | 11/1941 | Brainard | 24/562 |
| 2,498,372 | 2/1950 | Kortlucke, Jr. et al. | 24/518 |
| 2,818,871 | 1/1958 | Beaudry | 24/30.5 R |
| 2,897,825 | 8/1959 | Wagner . | |
| 3,094,807 | 6/1963 | Dorman . | |
| 3,523,534 | 8/1970 | Nolan | 24/518 |
| 3,551,965 | 1/1971 | Gordon | 24/30.5 R |
| 3,576,054 | 4/1971 | Rynk | 128/346 |
| 3,713,622 | 1/1973 | Dinger | 24/543 |
| 3,735,765 | 5/1973 | Ichelson | 24/518 |
| 3,824,654 | 7/1974 | Takabayashi . | |
| 3,874,042 | 4/1975 | Eddleman et al. . | |
| 3,978,555 | 9/1976 | Weisenthal | 24/543 |
| 4,212,303 | 7/1980 | Nolan | 24/562 |
| 4,264,047 | 4/1981 | Nelson | 248/73 |
| 4,296,529 | 10/1981 | Brown . | |

Primary Examiner—Victor N. Sakran
Attorney, Agent, or Firm—David I. Roche; T. W. Buckman

[57] ABSTRACT

An improved bag shut-off clamp is disclosed. The clamp comprises curved resilient first and second legs connected by an integral hinge. The clamp includes means for holding the ends of the first and second legs together for engaging transversely a closable bag having a neck interposable intermediate the first and second legs at the neck thereof for closing the bag at the neck. The clamp includes means for biasly urging opposed surfaces of the first and second legs engaging the neck substantially continuously together along the length thereof. The clamp further includes means for manually engaging the legs in biased relation. The clamp further includes means for localizing pressure along the length of the neck engaged between the legs, thereby sealingly closing the bag at the neck.

5 Claims, 18 Drawing Figures

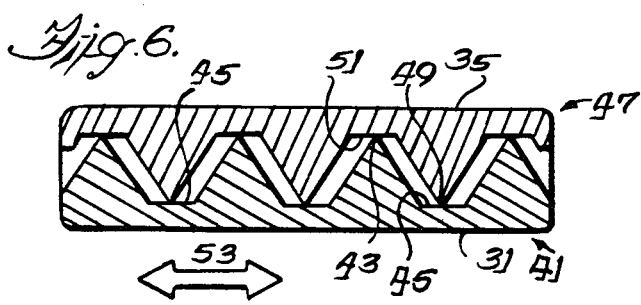
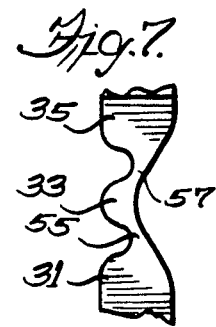
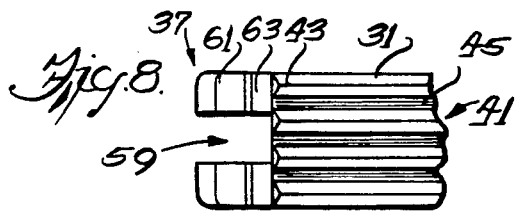
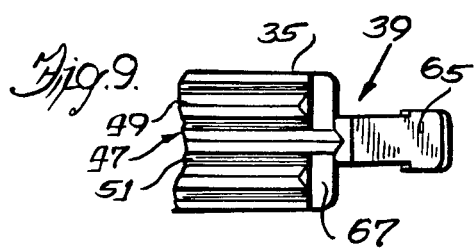
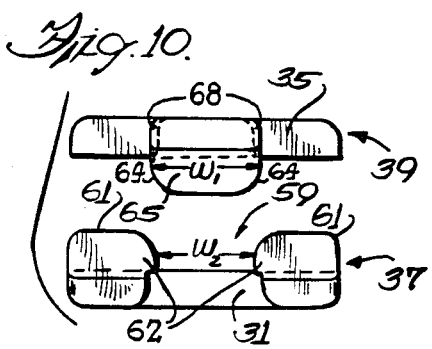
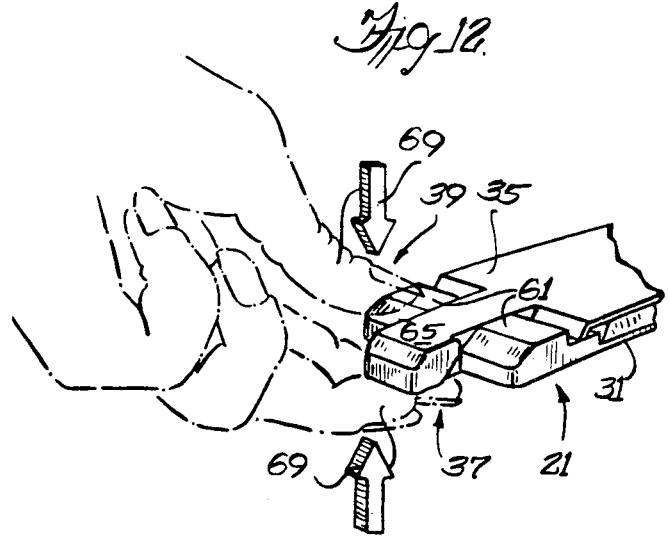
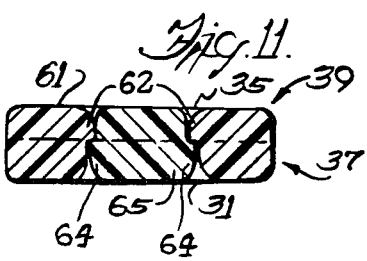
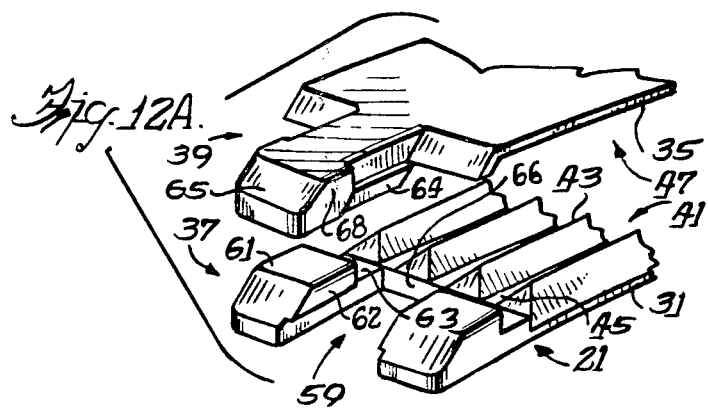

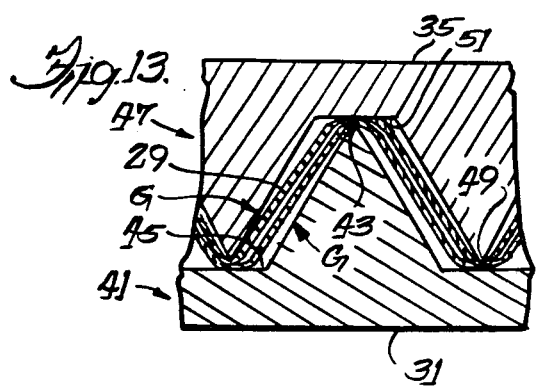
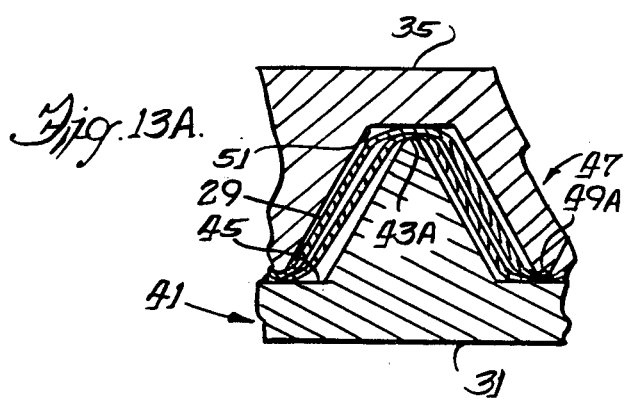
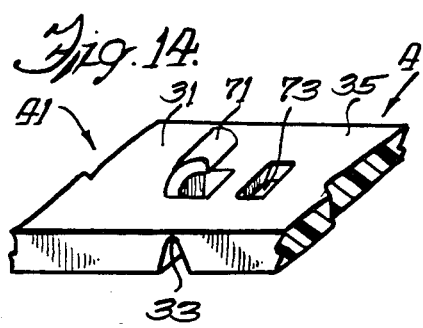
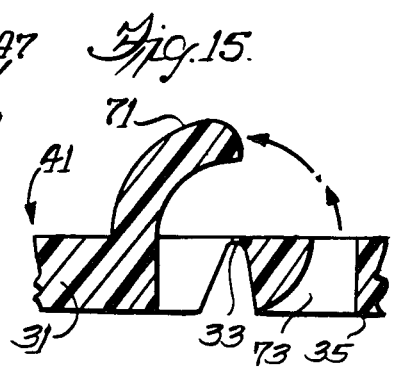
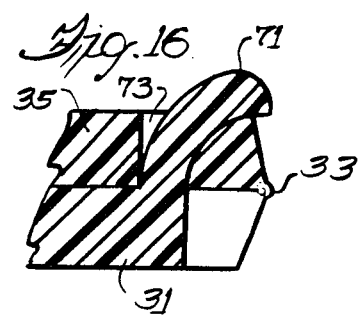

BAG SHUT-OFF CLAMP

BACKGROUND OF THE INVENTION

The instant application relates generally to a bag-closure clamp. More particularly, the instant invention is directed to a clamp useful in sealing ostomy bags.

Most ostomy bags are used by patients who have had, for example, colostomy, uterostomy, or like operations performed, whereby artificial passageways are formed through the human body.

Many colostomy patients, for example, make use of such an ostomy bag for the purpose of collecting soft or formed fecal material or urine or both. Such ostomy bags usually require bag-closure devices.

Most commerically available (prior art) bag-closure devices comprise, briefly, a first leg which is hingedly connected to a second leg. First end portions of the legs are usually connected together thereby providing each of the legs with a second or free-end portion. Many of these prior art devices also usually include a clasp, a hook, or other means for holding the free ends of the two legs relatively proximately together. See, for example, the U.S. Pat. No. 1,186,656 to Fridolph at page 1, lines 29-31 in connection with lines 47-54, or the U.S. Pat. No. 2,897,825 to Wagner at column 1, lines 58-60. Many of these clasps or hooks are difficult to manually manipulate.

It is well known that devices incorporating these mechanical features of elements have been used as barrettes for human hair (see, for example, the '825 patent at column 1, lines 15-17 in connection with lines 52-54), as clasps for clasping hair dressings, millinery, drapery or dresswear (see the '656 patent at page 1, lines 1-8 in connection with lines 76-79), or as adjusters for adjusting the length of belts or bands (see, for example, the U.S. Pat. No. 3,824,654 to Takabayashi at column 1, lines 3-8).

It is also well known, moreover, that many of the prior art devices which function principally as bag-closure devices are constructed such that when the legs of the bag-closure device are spread apart, a suitable balloon, bag, or envelope member having a neck (such an envelope member may include more than one opening) is generally transversely interposable therebetween at the neck thereof; and, after transverse interposition of the neck between the spread-out legs, the legs are urgeable together so that the clasp or holding means of the bag-closure device can be used to hold the two legs together, thereby securely holding the neck therebetween. In many prior art devices, the neck of the bag or envelope is held securely and initially sealed tightly so as to provide either an air-tight seal (see, for example, the U.S. Pat. No. 3,094,807 to Dorman, the U.S. Pat. No. 3,978,555 to Weisenthal, or the U.S. Pat. No. 4,296,529 to Brown) or a fluid-tight seal (see, for example, the U.S. Pat. No. 3,523,534 to Nolan, or the U.S. Pat. No. 3,874,042 to Eddleman et al).

For many closure devices where air or fluid tight sealing is a desideratum, it has been found, however, that the tight-sealing feature generally decays with time (i.e., such as would be caused by warpage or misalignment of the legs through use or aging) to where the closure device is no longer useful for the intended purpose.

For ostomy bag-closure devices it is a desideratum therefore that the device have a tight-sealing feature (as above described) which does not substantially decay with time. Additionally desirable features of such a bag-closure device are: (1) that the bag-closure device, when clamped, have a curvature which substantially conforms to the curvature of a predetermined region of the human body; (2) that the device, as it extends from the surface of the human body, be relatively thin so that it is substantially inconspicuous; (3) that the bag-closure device be able to accommodate a wide variety of bag thicknesses; and (4) that the device manually readily be clampable and openable, preferably with one hand.

OBJECTS AND SUMMARY OF THE INVENTION

Accordingly, it is a general object of this invention to provide a novel and improved bag shut-off clamp. A more specific object is to provide such a clamp which tightly seals a bag.

A related object is to provide such a clamp which is readily manually engageable with, disengageable from, and re-engageable with the bag.

A further object is to provide a clamp of such a size and shape that the clamp generally will not be noticeable when worn under clothing, the clamp conforming substantially to that region of the human body against which it lies.

Yet another object is to provide such a clamp which is substantially sealingly engageable with a variety of bags having various bag thicknesses.

Briefly, and in accordance with the foregoing objects, an improved bag shut-off clamp will now be summarized. Such a clamp comprises resilient first and second legs connected through an integral hinge. Such a clamp includes means for holding both of the second ends of the first and second legs together for engaging transversely a closable bag having a neck interposabale intermediate the first and second legs at the neck thereof for closing the bag at the neck. The clamp includes means for biasly urging opposed surfaces of the first and second legs engaging the neck substantially continuously together along the length thereof. The clamp further includes manually engageable means for manually engaging the legs in biased relation. The manually engageable means includes means for manually disengaging the legs from the neck engaged therebetween. The clamp further includes means for localizing pressure along the length of the neck engaged between the legs, thereby sealingly closing the bag at the neck.

BRIEF DESCRIPTION OF THE DRAWINGS

The foregoing, as well as other objects, features or advantages of the present invention will become more readily understood upon reading the following detailed description of the illustrated embodiments, together with reference to the drawings, wherein:

FIG. 6 is a sectional view, on an enlarged scale, presenting the touching engagement (of the legs) presented in FIG. 5, the view taken generally along the lines 6—6 in FIG. 5;

FIG. 7 is an edge view of the hinge, the view being presented on an enlarged scale and the clamp being rotated about 90 degrees in the counterclockwise sense about the hinge relative to FIG. 3;

FIG. 8 is a fragmentary top view (on an enlarged scale relative to FIG. 3) of a slot located at the distal end of the left arm of the clamp, the view taken generally along the lines 8—8 in FIG. 3;

FIG. 9 is a fragmentary top view, on an enlarged scale relative to FIG. 3, of a finger located at the distal end of the right arm of the clamp, the view taken generally along the lines 9—9 in FIG. 3;

FIG. 10 is a projected end-on view, on an enlarged scale relative to FIG. 4, of the distal end of the legs of the clamp, the view taken generally from the plane 10—10 in FIG. 4;

FIG. 11 is a sectional view of the clamping feature of the present invention taken along the plane 11—11 in FIG. 5.

FIG. 12 is an isometric view of the clamp presented in FIGS. 1-5, FIG. 12 presenting an easy-open feature of the clamp of the present invention;

FIG. 12A is an isometric view, partially in section, similar to the view presented in FIG. 12 but on an enlarged scale, showing the finger disengaged from the slot;

FIG. 13 is a fragmentary and partial sectional view, similar to the view of FIG. 6 but on an enlarged scale, of the clamp engaging a portion of a bag neck;

FIG. 13A is a fragmentary and partial sectional view, similar to the view of FIG. 13, of another embodiment of the clamp of the present invention;

FIG. 14 is a partial fragmentary view, in isometric, of yet another embodiment of the clamp of the present invention (on an enlarged scale relative to FIG. 3) presenting a leg-aligning feature;

FIG. 15 is a partial sectional view of the embodiment presented in FIG. 14 but on an enlarged scale, the view presenting the leg aligning feature of the clamp when the legs are in extended relation;

FIG. 16 is a partial sectional view, similar to the view presented in FIG. 15, showing the legs in proximate relation to each other.

DETAILED DESCRIPTION OF THE ILLUSTRATED EMBODIMENTS

Figure 1:
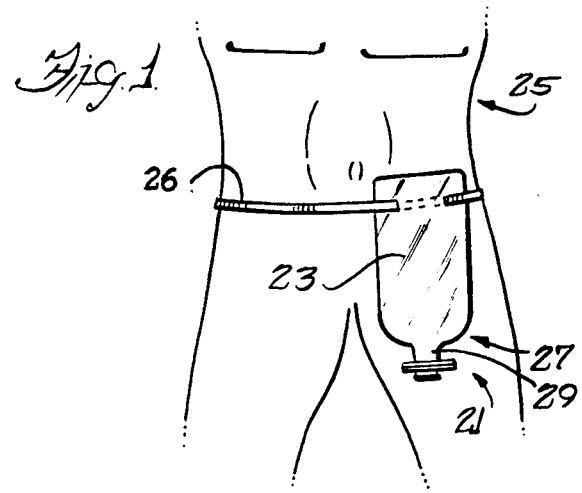
FIG. 1 is a frontal view of a portion of a human torso illustrating use of the improved clamp of the present invention functioning as a bag closure device.

Referring now to the drawings and initially to FIG. 1, it will be seen that the clamp 21 of the present invention is used preferably for sealing an ostomy bag 23. The illustrated ostomy bag 23 (FIG. 1) collects fluid of other material discharged from the wearer 25, via a bag inlet (not shown). The bag 23 includes a band 26 for securing the bag 23 to the wearer 25. A lower end 27 of the bag 23 includes a neck 29 through which the fluid flows when the clamp 21 is removed from the bag neck 29.

It will be seen, when viewing the clamp 21 on edge (FIG. 3), that the clamp 21 comprises a first elongated leg 31 which is integrally connected through a hinge 33 to a second elongated leg 35. Referring to FIG. 4, it will be seen that the first leg 31 has a first predetermined radius of curvature, R1, having a center located at C1. The second leg 35 has a second predetermined radius of curvature, R2, having a center located at C2. R2 is preferably greater than R1.

The improved clamp 21 is resilient; and distal ends 37, 39 (respectively) of the first and second legs 31, 35 (in relation to the hinge 33) are urgeable together (FIGS. 1, 4 and 5) by adult hand pressure.

Figure 2:
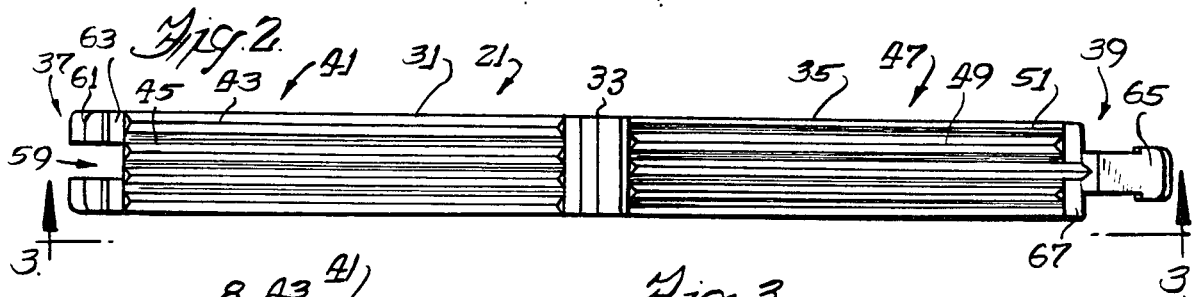
FIG. 2 is a top view (on an enlarged scale) of the clamp presented in FIG. 1.

A surface 41 of the first leg 31 has a plurality of (preferably four) raised surface projections 43 (see FIG. 6) which, when viewed from above (FIGS. 2, 8), appear as linear ridges, longitudinally arranged on the surface 41, each surface projection 43 appearing as substantially mutually parallel to the other surface projections 43. The surface 41 of the first leg 31 also includes a plurality of (preferably three) surface depressions 45 (see FIG. 6), each depression 45 being located between adjacent projections 43 (FIGS. 2, 6 and 8).

Figure 3:
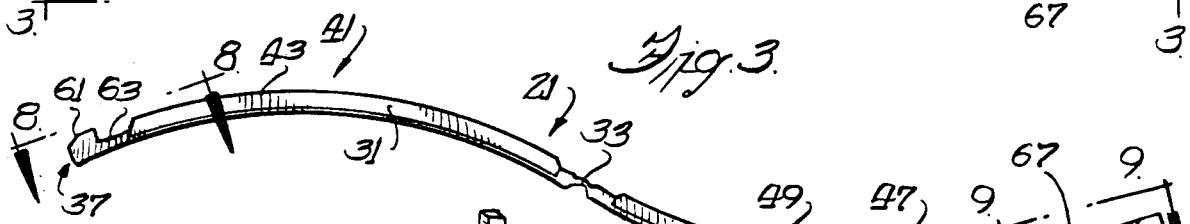
FIG. 3 is an edge view of the clamp, the view taken generally along the lines 3—3 in FIG. 2, illustrating an on-edge view of a hinge which connects two leg protions of the clamp.
Figure 4:
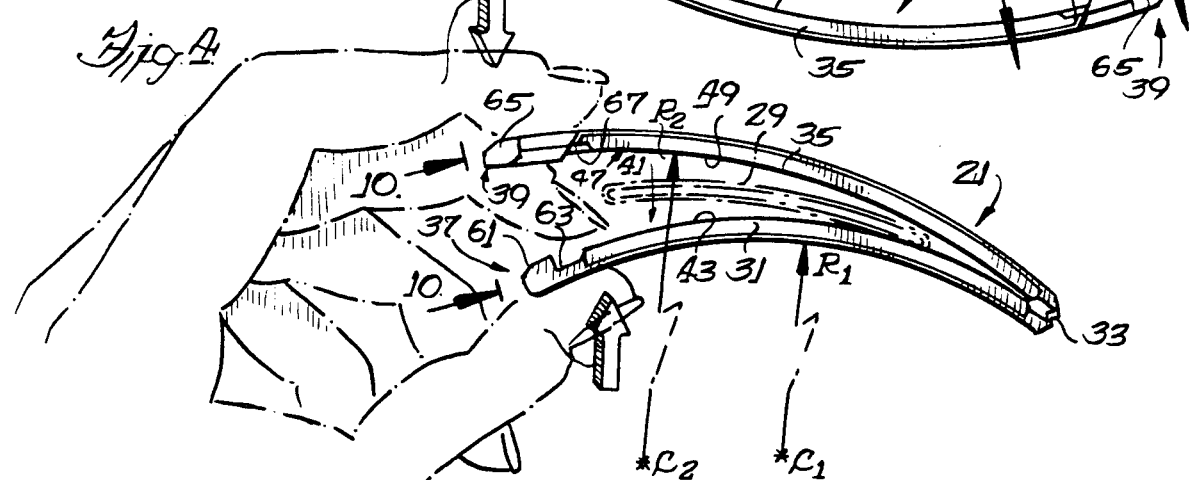
FIG. 4 is an edge view (similar to the view presented in FIG. 3) after the right or upper leg of the clamp has been pivoted in a counterclockwise sense about the hinge.

Although not directly viewable from FIGS. 3 and 4, it can be appreciated that the surface projections 43 and depressions 45 are curvilinear, and have a convex curvature relative to the surface 41 of the first leg 31. In one embodiment, the surface projections 43 are shown (FIGS. 6, 12A and 13) as having relatively sharp edges. In another embodiment, the surface projections 43A are shown (FIG. 13A) as having rounded edges.

The second leg 35 also includes a surface 47 which has a plurality of (preferably three) surface projections 49 and (preferably four) surface depressions 51 (see FIG. 6). The above-mentioned rounded edge embodiment, for example, is shown as having rounded surface projections 49A depending from the surface 47 of the upper leg 35 (see FIG. 13A). The surface projections 49 and depressions 51 of the second or upper leg 35, in sectional view (FIG. 6), are seen as being meshable respectively with the surface depressions 45 and projections 43 of the first or lower leg 31. In sectional view, the surface projections 43, 49 of the first and second legs 31, 35 (respectively) appear as relatively sharp teeth which alternatively touch the surface depressions 51, 45 (respectively) of the opposing first and second legs (35, 31).

The degree of roundness of the surface projections 43A, 49A is alterable. For a variety of reasons, it may be desirable for the clamp 21 to have rounded projections 43A, 49A (FIG. 13A). For example, it is desirable for the clamp 21 to have rounded projections 43A, 49A when there is a likelihood that sharp projections 43, 49 engaging the bag 23 would cause undesirable damage to the bag 23.

The surface projections 49 and depressions 51 of the second or upper leg 35 are curvilinear, and have a concave curvature relative to the surface 47 of the leg 35.

Referring to FIG. 6 it will be seen that as the meshable surfaces 41, 47 of the legs 31, 35 mesh, adjacent opposed projections 43, 49 preferably do not necessarily touch each other along the sides thereof because a relatively sharp portion of a projection 43 (in FIG. 6 refer, for example, to the first or lower leg 31 wherein the illustrated projection 43) is shown to make contact with a relatively flat depression 51 of the opposing leg (such as, for example, as is shown in FIG. 6 by the double-headed arrow 53) before touching of adjacent sides of opposing surface projections 43, 49 occurs.

As presented in FIG. 1, the improved clamp 21, as clamped to the neck 29, engages the upper thigh of the wearer 25. The first and second legs 31, 35 are joined to the hinge 33 at relatively narrow portions 55, 57 (FIG.

Figure 5:
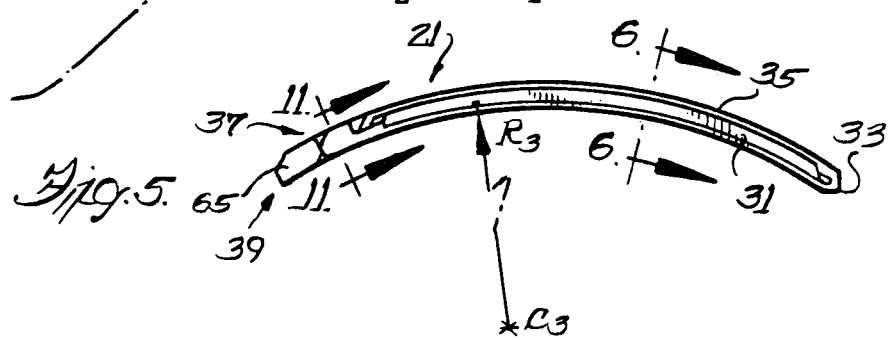
FIG. 5 is an edge view similar to the view presented in FIG. 4, but with the lower (formerly the left) and upper (formerly the right) legs brought into touching engagement.

7 so that a meshing contact (substantially continuously from the hinge 33 to the distal ends 37, 39) is made between the legs 31, 35 (FIG. 5).

The improved clamp 21 is made from a commercially available material which is preferably less likely to yield under pressure than is the material of the bag 23 (FIG. 13). Yet, the pressure exerted upon the bag 23 by the projections 43 of tone leg 31 engaging depressions 51 of the other leg 35 preferably do not cause puncturing, shearing, or any form of failure to the bag 23. Rather, before any damage is caused to the bag 23, individual projections 43 and depressions 51 prefereably yield slightly (FIG. 13) thereby presenting effective sealing of the bag 23 at the neck 29 without damaging the bag 23. A gap G between opposed sides of adjacent, oppositely-facing surface projections 43, 49 (FIG. 13) is preferably greater than the thickness of the bag neck 29, thereby providing for a relative degree of freedom of lateral movement (in the direction of the double-headed arrow 53, FIG. 6) of one leg (31, for example) relative to the other leg (35, for example) so that continuous sealing pressure (imposable upon the neck 29) is localizable to, and concentratable upon, the neck 29 at the regions where surface projections 43, 49 urge such portions of the neck 29 against opposing surface depressions 51, 45.

Also, resiliency of the clamp 21 is such that as the legs 31, 35 are urged together along the surfaces 41, 47 by hand pressure, the radii of curvature, R1, R2 of both legs 31, 35 are caused to change, whereby both legs 31, 35 are caused substantially to assume (approximately along the meshing surfaces 41, 47) a third radius of curvature, R3, having a center at C3 (FIG. 5). R3 is preferably less than R2 and preferably greater than R1. The third radius of curvature, R3, moreover, preferably matches substantially a predetermined curvature of a surface of the body, such as the upper thigh region (FIG. 1) against which the improved clamp 21 is intended to lie.

Several of the above described features of the clamp 21 co-act or otherwise cooperate so as to permit the clamp 21 to be usable to seal the neck 29 when the neck 29 is substantially transversely interposed intermediate (FIG. 1) the first and second legs 31, 35 (FIG. 4) and the surfaces 41, 47 are brought into engagement therewith (FIGS. 4, 5, 13 and 13A).

In addition to the closed clamp 21 having a predetermined radius of curvature R3 when in the meshing position (FIGS. 5, 10), the clamp 21 is relatively thin and extends only slightly from the thigh against which it is intended to lie (detail not shown). The relatively thin feature of the clamp 21 renders the clamp 21 substantially unnoticeable under clothing, in most situations.

The clamp 21 also includes a locking feature which permits relatively quick manual locking and unlocking of the clamp 21 with only one hand (FIG. 12). The distal end 37 of the leg 31 includes a substantially rectangular groove or slot 59 (FIG. 2) which is located intermediate a pair of shoulders 61. The shoulders 61 preferably extend slightly upwardly from the surface 41 of the leg 31 (FIGS. 3, 4). The slot 59 and shoulders 61 are separated from the surface projections 43 and surface depressions 45 of the leg 31 by a relatively shallow depression 63 (FIGS. 2, 3, 4, 8 and 12A) oriented generally transversely to the projections 43 and depressions 45.

The distal end 39 of the other leg 35 includes a finger 65 which extends generally outwardly relative to the hinge 33 (FIGS. 3, 4). The finger 65 is separated from the surface projections 49 and depressions 51 of the leg 35 by a relatively shallow depression 67 oriented generally transversely to the projections 49 and depressions 51 (FIG. 3).

A snap engageable feature of the clamp 21 will now be described. The forward (or lower) edge portion of the finger 65 (relative to the slot 59) has an effective width W1, which is generally slightly greater than a corresponding effective width, W2, located at the forward (or upper) edge portion of the slot 59 (relative to the finger 65). The lagging (or upper) edge portion of the finger 65 (relative to the slot 59) has a width which is preferably slightly less than W2 (see FIGS. 10, 11). The lagging (or lower) edge portion of the slot 59 (relative to the finger 65) has a width which is preferably slightly greater than W1. The shoulders 61 are equipped with inwardly projecting steps 62 occupying about the upper half of the surface of the shoulders which forms the slot 59. Mating steps 64 are formed about the lower half of the finger 65. The steps interlock to form a low profile snap-engageable feature which makes the clamp as inconspicious as possible. It should also be noted that relative curvature of the legs 31 and 35 and the location of the hinge 33 at the ends of the legs create tension in the outer leg 35 which results in improved clamping. In order to maintain the tension in the leg 35 the finger 65 has a pair of ears 68 which engage and bear against the end surfaces of the shoulders 61.

The resiliency of the clamp 21, however, is such that the finger 65 is urgeable into the slot 59 by hand pressure. As the finger 65 is urged into the slot 59 by hand pressure, generally in the direction of the arrows 69 (FIG. 12), the respective forward or leading portions of the finger 65 and slot 59 mutually yield so that the finger snaps into place in the slot 59 and is held there by a binding engagement with the sides of the shoulders 61 (FIG. 11).

The finger 65 is easily removable from the slot 59 by hand pressure. The finger 65 extends relatively greater outwardly from the hinge 33 than do the shoulders 61 (FIG. 5); and it is generally relatively easy to apply sufficient pressure to the clamp 21 using one hand (e.g., using the forefinger and thumb) in a manner so as to cause the finger 65 (held in place in the slot 59, FIGS. 5, 11) to be snapped out of the slot 59 (FIG. 10). In addition, the appropriate dimensions of the slot 59, shoulders 61, and finger 63 are such that the distal ends 37, 39 of the legs 31, 35 are easily locatable, engageable and disenageable, using one hand.

FIGS. 14–16 show an optional hinge reinforcing feature of the present invention. The integrally molded living hinge 33 may, after extended use, be prone to fatigue and ultimate failure. The need, therefore, may exist to prevent sudden failure of the hinge, especially if the clamp is used to seal a bag containing human waste where failure would be extremely disturbing and embarrassing to the wearer. The reinforcing feature includes an arcuate projection 71 extending generally outwardly from one of the legs toward the hinge 33 and an opening 73 in the other leg. The projection 71 and the opening 73 are shaped and aligned so that when the clamp is closed the projection locks into the opening. Failure of the hinge will then not result in failure of the clamp. One side of the opening 71 is curved to match the arc of the projection and the arc of the projection is, in turn, determined by its distance from the point about which the legs rotate, i.e., the hinge 33.

It can be appreciated by those skilled in the bag-closure art that the instant invention can either be used directly (or modified to be used) as a fluid-sealing tubing clamp, or as an air-tight sealing device for balloons, or in connection with a variety of flexible bags, such as bags used in connection with the storage of foodstuffs, chemicals, mechanical or electrical devices or parts thereof, garments, and the like. The instant invention moreover can be modified relatively easily and thereafter used, for example, as a barrette for hair, as a clasp for clasping hair, dressing, millinery, drapery, dresswear, and the like, or as an adjuster for belts, fans, and the like.

What has been illustrated and described herein is a novel clamp. While the clamp of the instant invention has been illustrated and described with reference to a preferred embodiment, the present invention is not limited thereto. On the contrary, alternatives, changes or modifications (in addition to the above-presented examples) may become apparent to those skilled in the art upon reading the foregoing description. Accordingly, such alternatives, changes or modifications are to be considered as forming a part of the invention insofar as they fall within the spirit and scope of the appended claims.

I claim:

1. A closure device comprising: first and second resilient curved legs connected to one another by an integrally formed hinge, said legs each having a first radius of curvature when said device is in an open position, said legs having a second radius of curvature not equal to said first radius of curvature when said device is in a closed position, said legs having substantially continuously intermeshing clamping surfaces, said legs having generally final radii of curvature in a closed position, said final radii of curvature having a finite value, said device having low-profile fastening means, said means comprising a single finger on at least one end of one of said legs and a pair of shoulders on at least one end of the other of said legs, said shoulders forming a slot dimensioned to snappingly engage said finger and hold said legs in clamping registration, said hinge having reinforcing means comprised of an arcuate prong located on one of said legs and a complimentary slot on the other of said legs, said prong and said slot adapted to engage one another upon closing of said device to prevent sudden failure of said hinge during use, each respective one of said first and second legs is arcuate, said first leg having a concave curvature and said second leg having a convex curvature respectively relative to said surfaces thereof, said first leg having a first radius of curvature, said second leg having a second radius of curvature, said first radius of curvature being relatively greater than said second radius of curvature; and wherein the resiliency of said closure device is such that said first and second legs are urgeable together substantially along said length of said surfaces by normal adult hand pressure thereby causing flexure of said first and second legs together, whereby said first and second legs are both thereby caused to assume a third radius, said third radius of curvature for said second leg having convex curvature along said surface thereof and being greater than said second radius of curvature, said third radius of curvature for said first leg having concave curvature along said surface thereof and being less than said first radius of curvature, said first and second legs when caused to assume said third radius of curvature being biasly urged together substantially continuously along the length of said surfaces thereof.

2. A closure device comprising: first and second resilient curved legs connected to one another by an integrally formed hinge, said legs each having a first radius of curvature when said device is in an open position, said legs having a second radius of curvature not equal to said first radius of curvature when said device is in a closed position, said legs having substantially continuously intermeshing clamping surfaces, said legs having generally final radii of curvature in a closed position, said final radii of curvature having a finite value, said device having low-profile fastening means, said means comprising a single finger on at least one end of one of said legs and a pair of shoulders on at least one end of the other of said legs, said shoulders forming a slot dimensioned to snappingly engage said finger and hold said legs in clamping registration, said hinge having reinforcing means comprised of an arcuate prong located on one of said legs and a complimentary slot on the other of said legs, said prong and said slot adapted to engage one another upon closing of said device to prevent sudden failure of said hinge during use, each respective one of said first and second legs has a plurality of surface projections extending outwardly from said respective surfaces thereof, a relative surface depression being located between adjacent surface projections for each one of said first and second legs, said projections and depressions of each respective one of said first and second legs being oriented substantially longitudinally along said length and located upon said respective surfaces such that said projections and said depressions of said first leg are mutually meshable respectively with said depressions and said projections of said second leg, each said projection of at least one of said first and second legs when touching said depression of the other one of said first and second legs thereby defining a gap between adjacent, oppositely facing projections of said surfaces so brought into touching engagement, whereupon each respective one of said projections and each respective one of said depressions of each respective one of said first and second legs cooperate such that after interposition of said neck intermediate said first and second legs and after said first and second legs are urged together, said projections, in the aggregate, of at least one of said first and second legs cause said neck to be urged substantially continuously against said depressions of the other one of said first and second legs, thereby providing in the aggregate substantially leakproof sealing of said neck engaged therebetween.

3. The closure device of claim 2 wherein said alignment means includes an arcuate projection integral at one end thereof with at least one of said first and second legs and having an opposite end thereof outwardly extending from said surface of said one of said first and second legs, the other one of said first and second legs including a through bore into which said arcuate projection is insertable, said through bore being spaced from said hinge and being located through said surface of said other one of said first and second legs in a manner such that engagement of said surfaces of said first and second legs causes said arcuate projection to become inserted into said through bore.

4. The closure device of claim 2 wherein said surface projections have sharp edges.

5. The closure device of claim 2 wherein said surface projections have rounded edges.

* * * * *